(12) United States Patent
Richter

(10) Patent No.: US 9,163,060 B2
(45) Date of Patent: Oct. 20, 2015

(54) TUBULIN INHIBITORS

(75) Inventor: Wolfgang Richter, Martinsried (DE)

(73) Assignee: R&D BIOPHARMACEUTICALS GMBH, Martinsreid (DE)

( * ) Notice: Subject to any disclaimer, the term of this patent is extended or adjusted under 35 U.S.C. 154(b) by 86 days.

(21) Appl. No.: 13/509,055

(22) PCT Filed: Nov. 12, 2010

(86) PCT No.: PCT/EP2010/006914
§ 371 (c)(1),
(2), (4) Date: Jun. 18, 2012

(87) PCT Pub. No.: WO2011/057805
PCT Pub. Date: May 19, 2011

(65) Prior Publication Data
US 2012/0252738 A1 Oct. 4, 2012

(30) Foreign Application Priority Data
Nov. 12, 2009 (EP) .................... 09014169

(51) Int. Cl.
A61K 38/00 (2006.01)
A61K 38/07 (2006.01)
C07K 5/02 (2006.01)
C07K 5/10 (2006.01)
A61P 35/00 (2006.01)
C07K 5/078 (2006.01)
C07K 5/00 (2006.01)
C07D 417/12 (2006.01)

(52) U.S. Cl.
CPC ............ *C07K 5/06139* (2013.01); *A61K 38/07* (2013.01); *C07D 417/12* (2013.01); *C07K 5/00* (2013.01); *C07K 5/02* (2013.01); *A61K 38/00* (2013.01)

(58) Field of Classification Search
USPC ......................................................... 514/1.1
See application file for complete search history.

(56) References Cited

U.S. PATENT DOCUMENTS

2005/0239713 A1* 10/2005 Domling et al. ............. 514/19

FOREIGN PATENT DOCUMENTS

| CN | 1890218 A | 1/2007 |
|---|---|---|
| CN | 101193884 A | 6/2008 |
| WO | WO 98/13375 | 4/1998 |
| WO | WO 2005/054199 A1 | 6/2005 |
| WO | WO 2006/138180 A1 | 12/2006 |
| WO | WO 2008/138561 | 11/2008 |
| WO | WO 2009/012958 | 1/2009 |
| WO | WO 2009/055562 | 4/2009 |

OTHER PUBLICATIONS

Patterson et al. "Design, Synthesis, and Biological Properties of Highly Potent Tubulysin D Analogues" Chemistry—A European Journal 2007 13:9534-9541.
Sasse et al. "Tubulysins, New Cytostatic Peptides from Myxobacteria Acting on Microtubuli" The Journal of Antibiotics 2000 53(9):879-885.
Strotmann et al. "The Dehydrogenase Assay with Resazurin: Practical Performance as a Monitoring System and Ph-Dependent Toxicity of Phenolic Compounds" Ecotoxicology and Environmental Safety 1993 25:79-89.
International Search Report from PCT/EP2010/006914, Dec. 9, 2010.
International Preliminary Report on Patentability from PCT/EP2010/006914, May 15, 2012.

* cited by examiner

*Primary Examiner* — Karlheinz R Skowronek
*Assistant Examiner* — Catherine Mader
(74) *Attorney, Agent, or Firm* — Licata & Tyrrell P.C.

(57) ABSTRACT

The present invention relates to novel tubulin binding molecules of formula (I) and their use for the treatment of cancer and other diseases.

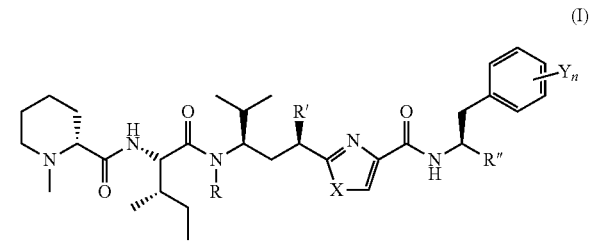

10 Claims, No Drawings

TUBULIN INHIBITORS

This application is a U.S. National Stage Application of PCT/EP2010/006914 filed Nov. 12, 2010, which claims priority from EPO Application No. 09014169.8 filed Nov. 12, 2009, the contents of each of which are incorporated herein by reference in their entirety.

The present invention refers to a novel class of cytotoxic molecules and their use for the treatment of cancer and other diseases.

It is an objective of the present invention to provide novel cytotoxic molecules with a highly potent activity against cancer cell lines.

The present invention provides one or more compounds of formula (I):

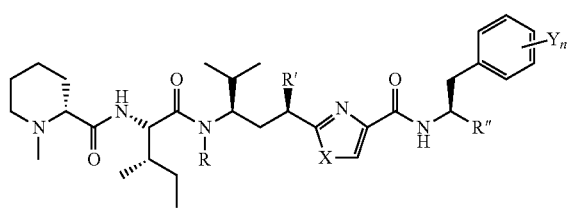

wherein
R is an alkyl, alkenyl, alkynyl, CO-alkyl, heteroalkyl, aralkyl or heteroaralkyl group, all of which may optionally be substituted;
R' is OH, an alkyl, alkenyl, alkynyl, —O—CO-alkyl or heteroalkyl group, all of which may optionally be substituted;
R" is a group of formula $CO_2H$, $CO_2R'''$, CONHR''' or $CONR_2'''$, with R''' independently being an alkyl, aryl, aralkyl or heteroalkyl group;
X is S or O;
Y is independently optionally substituted alkyl, optionally substituted heteroalkyl, halogen, CN, $NO_2$ or OH;
n is 0, 1, 2, 3, 4 or 5;
or a pharmacologically acceptable salt, solvate, hydrate or a pharmacologically acceptable formulation thereof.

The expression alkyl refers to a saturated, straight-chain or branched hydrocarbon group that contains from 1 to 20 carbon atoms, preferably from 1 to 12 carbon atoms, especially from 1 to 6 (e.g. 1, 2, 3 or 4) carbon atoms, for example methyl, ethyl, propyl, isopropyl, isobutyl, n-butyl, sek-butyl, tert-butyl, n-pentyl, 2,2-dimethylpropyl, 2-methylbutyl, n-hexyl, 2,2-dimethylbutyl or 2,3-dimethylbutyl.

The expressions alkenyl and alkynyl refer to at least partially unsaturated, straight-chain or branched hydrocarbon groups that contain from 2 to 20 carbon atoms, preferably from 2 to 12 carbon atoms, especially from 2 to 6 (e.g. 2, 3 or 4) carbon atoms, for example an ethenyl, allyl, acetylenyl, propargyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atoms (e.g. 1, 2 or 3 hydrogen atoms) have been replaced by a halogen atom (preferably F or Cl) such as, for example, a 2,2,2-trichloroethyl or a trifluoromethyl group.

The expression heteroalkyl refers to an alkyl, alkenyl or alkynyl group in which one or more (preferably 1, 2 or 3) carbon atoms have been replaced by an oxygen, nitrogen, phosphorus, boron, selenium, silicon or sulfur atom (preferably by an oxygen, sulfur or nitrogen atom). The expression heteroalkyl furthermore refers to a carboxylic acid or to a group derived from a carboxylic acid, such as, for example, acyl acylalkyl, alkoxycarbonyl, acyloxy, acyloxyalkyl, carboxyalkylamide or alkoxycarbonyloxy.

Preferably, a heteroalkyl group contains from 1 to 12 carbon atoms and from 1 to 4 hetero atoms selected from oxygen, nitrogen and sulphur (especially oxygen and nitrogen). Especially preferably, a heteroalkyl group contains from 1 to 6 (e.g. 1, 2, 3 or 4) carbon atoms and 1, 2 or 3 (especially 1 or 2) hetero atoms selected from oxygen, nitrogen and sulphur (especially oxygen and nitrogen)

Examples of heteroalkyl groups are groups of formulae: $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—$R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ is a hydrogen atom, a $C_1$-$C_6$ alkyl, a $C_2$-$C_6$ alkenyl or a $C_2$-$C_6$ alkynyl group; $R^b$ is a hydrogen atom, a $C_1$-$C_6$ alkyl, a $C_2$-$C_6$ alkenyl or a $C_2$-$C_6$ alkynyl group; $R^c$ is a hydrogen atom, a $C_1$-$C_6$ alkyl, a $C_2$-$C_6$ alkenyl or a $C_2$-$C_6$ alkynyl group; $R^d$ is a hydrogen atom, a $C_1$-$C_6$ alkyl, a $C_2$-$C_6$ alkenyl or a $C_2$-$C_6$ alkynyl group and $Y^a$ is a direct bond, a $C_{1-6}$ alkylene, a $C_2$-$C_6$ alkenylene or a $C_2$-$C_6$ alkynylene group, wherein each heteroalkyl group contains at least one carbon atom and one or more hydrogen atoms may be replaced by halogen (e.g. fluorine or chlorine) atoms.

Specific examples of heteroalkyl groups are methoxy, trifluoromethoxy, ethoxy, n-propyloxy, isopropyloxy, tert-butyloxy, methoxymethyl, ethoxymethyl, —$CH_2CH_2OH$, —$CH_2OH$, —$CH_2CH_2SH$, —$CH_2SH$, —$CH_2CH_2SSCH_2CH_2NH_2$, —$CH_2CH_2SSCH_2CH_2COOH$, methoxyethyl, methylamino, ethylamino, dimethylamino, diethylamino, isopropylethylamino, methylamino methyl, ethylamino methyl, diisopropylamino ethyl, enol ether, dimethyl-amino methyl, dimethylamino ethyl, acetyl, propionyl, butyryloxy, acetyloxy, methoxycarbonyl, ethoxycarbonyl, N-ethyl-N-methylcarbamoyl or N-methylcarbamoyl. Further examples of heteroalkyl groups are nitrile, isonitrile, cyanate, thio-cyanate, isocyanate, isothiocyanate and alkylnitrile groups.

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, $=$O, SH, $=$S, $NH_2$, $=$NH, $N_3$ or $NO_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression heterocycloalkyl refers to a cycloalkyl group as defined above in which one or more (preferably 1, 2 or 3) ring carbon atoms, each independently, have been replaced by an oxygen, nitrogen, silicon, selenium, phosphorus or sulfur atom (preferably by an oxygen, sulfur or nitrogen atom). A heterocycloalkyl group has preferably 1 or 2 ring(s) containing from 3 to 10 (especially 3, 4, 5, 6 or 7) ring atoms (preferably selected from C, O, N and S). The expression heterocycloalkyl refers furthermore to groups in which one or more hydrogen atoms have been replaced by fluorine, chlorine, bromine or iodine atoms or by OH, $=$O, SH, $=$S, $NH_2$, $=$NH, $N_3$ or $NO_2$ groups. Examples are a piperidyl, prolinyl, imidazolidinyl, piperazinyl, morpholinyl, urotropinyl, pyrrolidinyl, tetrahydrothiophenyl, tetrahydropyranyl, tetrahydrofuryl or 2-pyrazolinyl group and also lactames, lactones, cyclic imides and cyclic anhydrides.

The expression alkylcycloalkyl refers to a group that contains both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two ring systems having from 3 to 10 (especially 3, 4, 5, 6 or 7) ring carbon atoms, and one or two alkyl, alkenyl or alkynyl groups having 1 or 2 to 6 carbon atoms.

The expression heteroalkylcycloalkyl refers to alkylcycloalkyl groups as defined above in which one or more (preferably 1, 2 or 3) carbon atoms, each independently, have been replaced by an oxygen, nitrogen, silicon, selenium, phosphorus or sulfur atom (preferably by an oxygen, sulfur or nitrogen atom). A heteroalkylcycloalkyl group preferably contains 1 or 2 ring systems having from 3 to 10 (especially 3, 4, 5, 6 or 7) ring atoms, and one or two alkyl, alkenyl, alkynyl or heteroalkyl groups having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being saturated or mono-, di- or tri-unsaturated.

The expression aryl or Ar refers to an aromatic group that contains one or more rings containing from 6 to 14 ring carbon atoms, preferably from 6 to 10 (especially 6) ring carbon atoms. The expression aryl (or Ar, respectively) refers furthermore to groups in which one or more hydrogen atoms have been replaced by fluorine, chlorine, bromine or iodine atoms or by OH, SH, $NH_2$, $N_3$ or $NO_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, preferably from 5 to 10 (especially 5 or 6) ring atoms, and contains one or more (preferably 1, 2, 3 or 4) oxygen, nitrogen, phosphorus or sulfur ring atoms (preferably O, S or N). The expression heteroaryl refers furthermore to groups in which one or more hydrogen atoms have been replaced by fluorine, chlorine, bromine or iodine atoms or by OH, SH, $N_3$, $NH_2$ or $NO_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3"-bifuryl, pyrazolyl (e.g. 3-pyrazolyl) and isoquinolinyl groups.

The expression aralkyl refers to a group containing both aryl and also alkyl, alkenyl, alkynyl and/or cycloalkyl groups in accordance with the above definitions, such as, for example, an arylalkyl, arylalkenyl, arylalkynyl, arylcycloalkyl, arylcycloalkenyl, alkylarylcycloalkyl and alkylarylcycloalkenyl group. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to an aralkyl group as defined above in which one or more (preferably 1, 2, 3 or 4) carbon atoms, each independently, have been replaced by an oxygen, nitrogen, silicon, selenium, phosphorus, boron or sulfur atom (preferably oxygen, sulfur or nitrogen), that is to say to a group containing both aryl or heteroaryl, respectively, and also alkyl, alkenyl, alkynyl and/or heteroalkyl and/or cycloalkyl and/or heterocycloalkyl groups in accordance with the above definitions. A heteroarylkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, wherein 1, 2, 3 or 4 of these carbon atoms have been replaced by oxygen, sulfur or nitrogen atoms.

Examples are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkyl, heteroarylheteroalkylcycloalkyl, heteroarylheteroalkylcycloalkenyl and heteroarylheteroalkylheterocycloalkyl groups, the cyclic groups being saturated or mono-, di- or tri-unsaturated. Specific examples are, a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

The term "optionally substituted" relates to groups, wherein one or more hydrogen atoms have been replaced by fluorine, chlorine, bromine or iodine atoms or by OH, =O, SH, =S, $NH_2$, =NH or $NO_2$ groups. This term relates further to groups, which can be exclusively or additionally substituted with unsubstituted $C_1$-$C_6$ alkyl, $C_2$-$C_6$ alkenyl, $C_2$-$C_6$ alkinyl or $C_1$-$C_6$ heteroalkyl groups.

Protecting groups are known to a person skilled in the art and e.g. described in P. J. Kocienski, Protecting Groups, Georg Thieme Verlag, Stuttgart, 1994 and in T. W. Greene, P. G. M. Wuts, Protective Groups in Organic Synthesis, John Wiley & Sons, New York, 1999. Common amino protecting groups are e.g. t-butyloxycarbonyl (Boc), t-butyldimethylsilyl (TBS), benzyloxycarbonyl (Cbz, Z), benzyl (Bn), benzoyl (Bz), fluorenylmethyloxycarbonyl (Fmoc), allyloxycarbonyl (Alloc), triethylsilyl (TES), trichlorethyloxycarbonyl (Troc), acetyl or trifluoracetyl.

Compounds of formula (I) may comprise several chiral centers depending on their substitution pattern. The present invention relates to all defined enantio- and diastereoisomers as well as their mixtures in all ratios. Moreover the present invention relates to all cis/trans isomers of compounds of general formula (I) as well as their mixtures. Moreover the present invention relates to all tautomeric forms of compounds of the general formula (I).

Preferably, R is $C_1$-$C_6$ alkyl; especially a methyl, ethyl, propyl, butyl, isopropyl, isobutyl, n-pentyl or n-hexyl.

Preferably, R' is —O—CO-alkyl, alkyl or heteroalkyl (e.g. —O-alkyl, —O-alkyl-O-alkyl), especially O-Acetyl (OAc, $OCOCH_3$), —O-propyl or —$OCH_2OCH_3$.

Preferably, R" is a group of formula $CO_2H$ or $CO_2R'''$, with R''' preferably being an alkyl group.

Preferably X is S.

Preferably Y is independently optionally substituted alkyl, halogen (e.g. F or Cl) or OH.

Preferably n is 0, 1, 2 or 3, especially 0 or 1.

Especially preferred are compounds of formula (I) wherein:
R is $C_1$-$C_6$ alkyl, especially —$CH_3$, ethyl, propyl or butyl;
R' is —O—CO-alkyl or heteroalkyl, especially —O—CO—$CH_3$, —O-propyl or —$OCH_2OCH_3$;
R" is —$CO_2H$ or —$CO_2R'''$, with R''' being a alkyl group;
X is S;
Y is independently optionally substituted alkyl, halogen (e.g. F or Cl) or OH; and
n is 0 or 1.

Examples of pharmacologically acceptable salts of compounds of formula (I) are salts of physiologically acceptable mineral acids, such as hydrochloric acid, sulfuric acid and phosphoric acid, or salts of organic acids, such as methanesulfonic acid, p-toluenesulfonic acid, lactic acid, formic acid acetic acid, trifluoroacetic acid, citric acid, succinic acid, fumaric acid, maleic acid and salicylic acid. Further examples of pharmacologically acceptable salts of the compounds of formula (I) are alkali metal and alkaline earth metal salts such as, for example, sodium, potassium, lithium, calcium or magnesium salts, ammonium salts or salts of organic bases such as, for example, methylamine, dimethylamine, triethylamine, piperidine, ethylenediamine, lysine, choline hydroxide, meglumine, morpholine or arginine salts. Compounds of formula (I) may be solvated, especially hydrated. The hydration may take place, for example, during the preparation process or as a consequence of the hygroscopic nature of the initially anhydrous compounds of formula (I). The solvates and/or hydrates may e.g. be present in solid or liquid form.

The therapeutic use of compounds of formula (I), their pharmacologically acceptable salts, solvates and hydrates, respectively, as well as formulations and pharmaceutical compositions also lie within the scope of the present invention.

The pharmaceutical compositions according to the present invention comprise at least one compound of formula (I) as an active ingredient and, optionally, carrier substances and/or adjuvants.

The use of compounds of formula (I) for the preparation of medicaments for the treatment and/or prevention of cancer or other diseases is also subject of the present invention. Moreover, the present compounds are of interest for the prevention and/or treatment of tumor diseases.

Cancers that can be treated or prevented by the compositions and methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumour, cervical cancer, testicular tumour, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukaemia and acute myelocytic leukaemia (myeloblastic, promyelocytic, myelomonocytic, monocytic and erythroleukemia); chronic leukaemia (chronic myelocytic (granulocytic) leukaemia and chronic lymphocytic Leukaemia), and polycythemia vera, lymphoma (Hodgkin's disease and non-Hodgkin's disease), multiple myeloma. Waldenstrohm's macroglobulinemia, and heavy chain disease.

Other examples of leukaemias include acute and/or chronic leukaemias, e.g., lymphocytic leukaemia (e.g., as exemplified by the p388 (murine) cell line), large granular lymphocytic leukaemia, and lymphoblastic leukaemia; T-cell leukaemias, e.g., T-cell leukaemia (e.g., as exemplified by the CEM, Jurkat, and HSB-2 (acute), YAC 1 (murine) cell lines), T-lymphocytic leukaemia, and T-lymphoblastic leukaemia; B cell leukaemia (e.g., as exemplified by the SB (acute) celline), and B-lymphocytic leukaemia; mixed cellieukaemias, e.g., B and T cellieukaemia and B and T lymphocytic leukaemia: myeloid leukaemias, e.g., granulocytic leukaemia, myelocytic leukaemia (e.g., as exemplified by the HL-60 (promyelocyte) cell line), and myelogenous leukaemia (e.g., as exemplified by the K562 (chronic) celline); neutrophilic leukaemia; eosinophilic leukaemia: monocytic leukaemia (e.g., as exemplified by the THP-1 (acute) celline); myclomonocytic Leukaemia; Naegeli-type myeloid leukaemia; and non-lymphocytic leukemia. Other examples of leukaemias are described in Chapter 60 of The Chemotherapy Sourcebook, Michael C. Perry Ed., Williams & Williams (1992) and Section 36 of Holland Frie Cancer Medicine 5th Ed., Bast et al. Eds., B. C. Decker Inc. (2000). The entire teachings of the preceding references are incorporated herein by reference.

In general, compounds of formula (I) can be given as a single treatment or as multiple treatments either alone or in combination with an arbitrary therapeutic substance according to known and accepted modes or as a continuous treatment whereby the active principle can be embedded in a matrix such as e.g. an implantable hydrogel. Compositions according to the invention can be administered in one of the following ways: orally, including dragees, coated tablets, pills, semi-solids, soft or hard capsules, solutions, emulsions or suspensions; parenteral, including injectable solutions; rectal as suppositories; by inhalation, including powder formulation or as a spray, transdermal or intranasal. For the production of such tablets, pills, semi solids, coated tabletts, dragees and hard gelatine capsules the therapeutically used product is mixed with pharmacologically inert, inorganic or organic carriers, e.g. with lactose, sucrose, glucose, gelatine, malt, silica gel, starch, or derivatives thereof, talkum, stearinic acid or its salts, dried skim milk and the like. For the production of soft capsules one may use carriers like vegetable oils, petroleum, animal or synthetic oils, wax, fat, polyols. For the production of liquid solutions and syrups one may use carriers for example water, alcohols, aqueous saline, aqueous dextrose, polyole, glycerin, vegetable oils, petroleum, animal or synthetic oils. For the production of suppositories one may use excipients like e.g. vegetable, petroleum, animal or synthetic oils, wax, fat and polyols. For aerosol formulations one may use compressed gases suitable for this purpose like e.g. oxygen, nitrogen, noble gas and carbon dioxide. The pharmaceutically useful agents may also contain additives for conservation, stabilisation, e.g. UV stabilizer, emulsifier, sweetener, aromatiser, salts to change the osmotic pressure, buffers, coating additives and antioxidants.

Combinations with other therapeutic agents can include further agents, which are commonly used to treat the diseases mentioned above, especially tumor diseases.

It has been surprisingly found that the compounds of the present invention show the same or a very similar biological activity as the known Tubulysins (see e.g. WO 9813375; F. Sasse, H. Steinmetz, G. Höfle, H. Reichenbach, J. Antibiot. 2000, 53, 879-885; A. W. Patterson et al, Chem. Eur. J. 2007, 13, 9534-9541), although the "Tup" unit has been replaced by a phenylalanine derivative, a much simpler structural unit which is much less complicated to synthesize. The replacement of the "Tup" unit by a natural amino acid makes the overall compounds more peptide-like which improves the biodegradability of the compounds in the body. Furthermore, this replacement leads to a reduction of the overall weight of the resulting compounds which leads to an enhanced bioavailability. In addition, the new compounds show an enhanced binding to tubulin.

EXAMPLES

According to the synthetic procedures of the building blocks disclosed herein, compounds of formula (I) were synthesized using common peptide coupling methods known to a person skilled in the art.

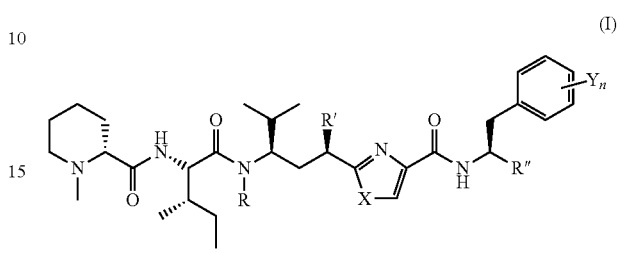

(I)

Compounds of formula (I) having the following residues where prepared:
R: H, methyl, propyl;
R': OAcetyl, —OCH$_2$OCH$_3$;
R": —CO$_2$H, —CO$_2$CH$_3$; —CONHCH$_2$CH$_2$OH
X: S;
Y: H, F, OH;
n: 0, 1.

These compounds are especially preferred.

Synthetic Procedures

The syntheses of the respective building blocks used for the preparation of the compounds of formula (I) were performed according to procedures described in PCT/EP2008/003762 (WO 2008/138561). All compounds described in this patent were characterized by $^1$H-NMR, $^{13}$C-NMR and mass spectroscopy. The purity was identified by HPLC.

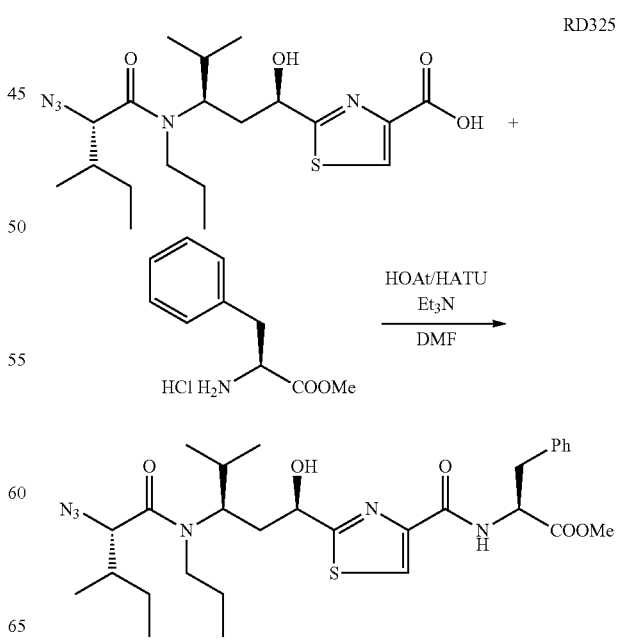

RD325

To a solution of the dipeptide (150 mg, 0.35 mmol) in DMF (5 mL) HOAt (57 mg, 0.42 mmol), HATU (160 mg, 0.42 mmol) and Et₃N (107 μL, 0.77 mmol) were added. After stirring for 5 min Phenylalaninmethylester as hydrochloride salt (84 mg, 0.39 mmol) was added. The reaction mixture was stirred for 2 h. The reaction was diluted with H₂O (10 mL) and extracted with Et₂O (1×10 mL). The organic phase was washed with a 1N aqueous solution of HCl (1×15 mL), with a saturated aqueous solution of NaHCO₃ (1×15 mL) and with brine (2×15 mL). After drying over anhydrous Na₂SO₄, and filtration, the solvent was removed in vacuo to give 176 mg of pure RD325 (86 t yield) as a white foam.

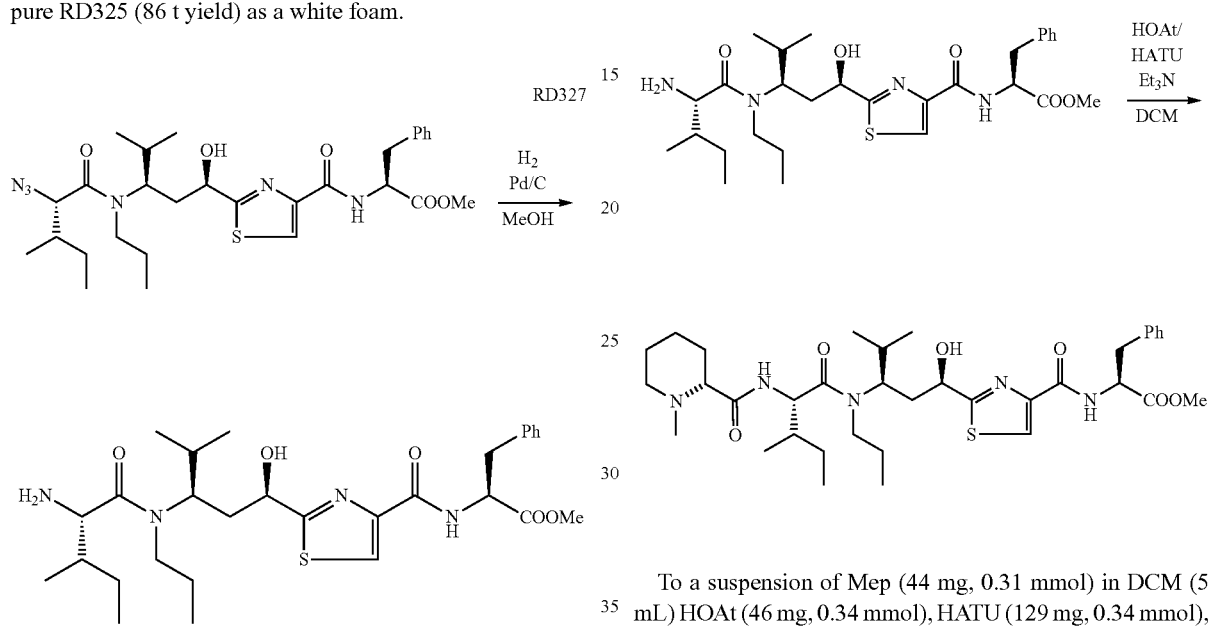

To a solution of RD325 (166 mg, 0.28 mmol) in MeOH (5 mL) Pd/C was added. The reaction mixture was stirred 18 h under a hydrogen atmosphere. The reaction was filtered through celite and the filtrate was concentrated under reduced pressure to give 157 mg of pure RD327 (quantitative yield) as a white foam.

To a suspension of Mep (44 mg, 0.31 mmol) in DCM (5 mL) HOAt (46 mg, 0.34 mmol), HATU (129 mg, 0.34 mmol), Et₃N (86 μL, 0.62 mmol) and RD327 (157 mg, 0.28 mmol) were added. The reaction mixture was stirred for 4 h. The reaction was washed with H₂O (10 mL), with a saturated aqueous solution of NaHCO₃ (1×15 mL) and with brine (1×15 mL). After drying over anhydrous Na₂SO₄, and filtration, the solvent was removed in vacuo. The crude was purified by FC (DCM:MeOH 95:5) to give 178 mg of RD329 (92% yield) as a white foam.

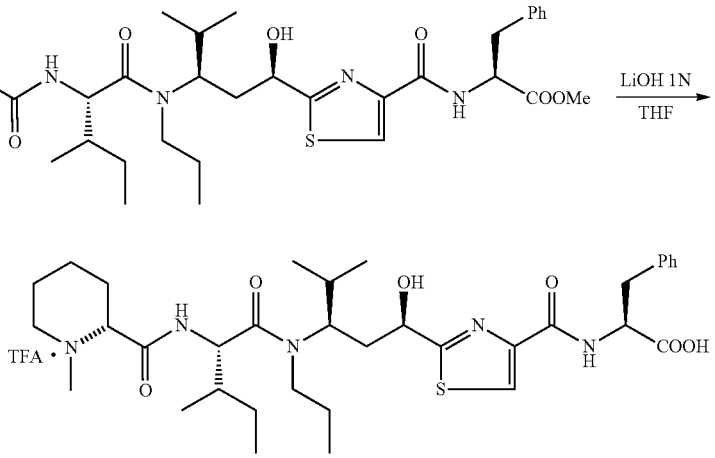

To a solution of RD329 (168 mg, 0.24 mmol) in THF (5 mL) a 1N aqueous solution of LiOH (720 μL, 0.72 mmol) was added. The reaction was stirred for 18 h and then acidified with TFA until pH 1-2 was reached. The resulting mixture was washed with H₂O (5 mL) and extracted with AcOEt (10 mL). The organic phase was dried over anhydrous Na₂SO₄, filtered and the solvent was removed in vacuo. The residue was purified by FC (DCM/MeOH 9:1), affording 169 mg of RD331 (90% yield) as a white foam.

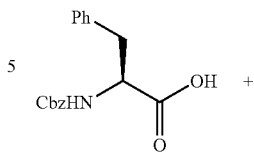

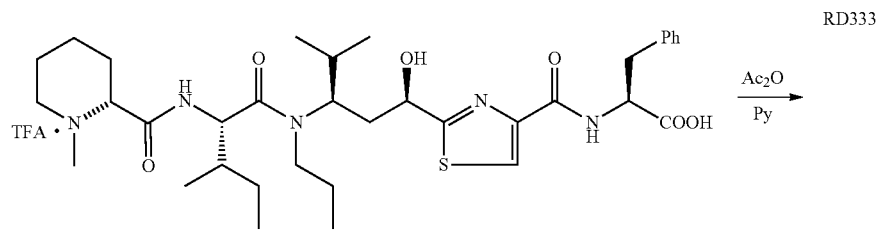

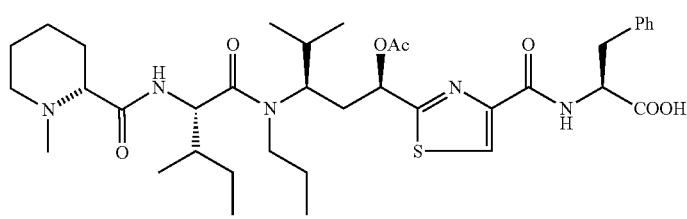

To a solution of RD331 (157 mg, 0.20 mmol) in pyridine (4 mL) Ac₂O (2 mL) was added and the solution was stirred overnight. The solvent was removed in vacuo and the crude product was purified by FC (DCM:MeOH 98:2, 9:1) and by reverse phase HPLC to give 25 mg of RD333 (16% yield).

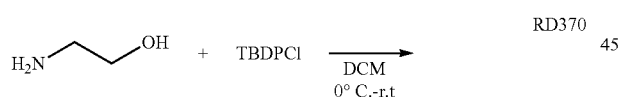

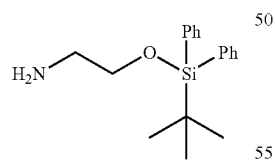

To a solution of ethanolamine (0.603 mL, 10 mmol) in DCM (5 mL), cooled at 0° C., TBDPCl was added (260 7 μL, 1 mmol). The reaction mixture was warmed to r.t., stirred overnight and quenched with water (5 mL). The layers were separated and the organic phase dried over anhydrous Na₂SO₄, filtered and the solvent was removed in vacuo. The residue was purified by FC (DCM/MeOH 9:1), affording 154 mg of RD370 (51% yield) as a colorless oil.

-continued

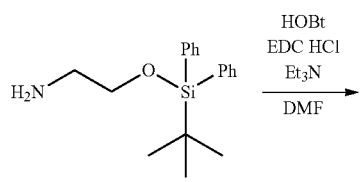

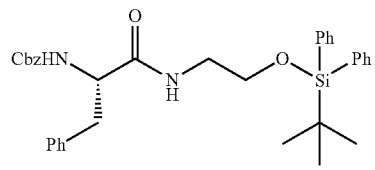

To a solution of the protected Phenylalanine (183 mg, 0.61 mmol) in DMF (5 mL) HOBt (89 mg, 0.66 mmol), EDC HCl (126 mg, 0.66 mmol) and Et₃N (163 μL, 1.17 mmol) were added. After stirring for 5 min RD370 (154 mg, 0.51 mmol) was added. The reaction mixture was stirred for 2 h. The reaction was diluted with H₂O (10 mL) and extracted with Et₂O (1×10 mL). The organic phase was washed with a saturated aqueous solution of NaHCO₃ (1×15 mL) and with brine (2×15 mL). After drying over anhydrous Na₂SO₄, and filtration, the solvent was removed in vacuo. The residue was purified by FC (Hex/AcOEt 75:25) to give 258 mg of RD373 (87% yield) as a white foam.

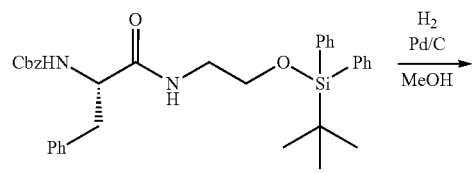

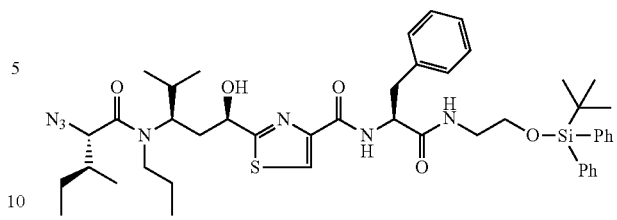

RD375

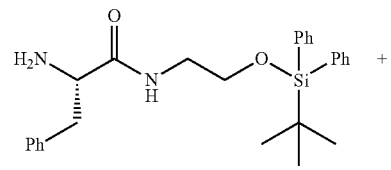

+

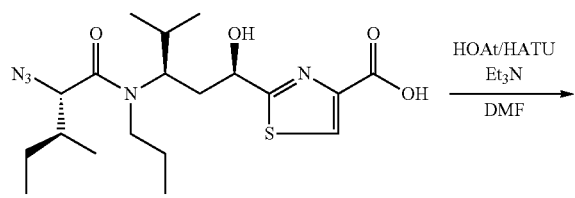

To a solution of RD373 (248 mg, 0.43 mmol) in MeOH (5 mL) Pd/C was added. The reaction mixture was stirred 18 h under a hydrogen atmosphere. The reaction was filtered through celite and the filtrate was concentrated under reduced pressure to give 178 mg of amine (93% yield) as a colorless oil. To a suspension of dipeptide (65 mg, 0.15 mmol) in DMF (5 mL) HOAt (25 mg, 0.18 mmol), HATU (68 mg, 0.18 mmol), Et$_3$N (46 µL, 0.33 mmol) and amine (80 mg, 0.18 mmol) were added. The reaction mixture was stirred for 4 h and 20 mL Et$_2$O were added. The reaction was washed with H$_2$O (10 mL), with a saturated aqueous solution of NaHCO$_3$ (1×15 mL) and with brine (1×15 mL). After drying over anhydrous Na$_2$SO$_4$, and filtration, the solvent was removed in vacuo to give 127 mg of pure RD375 (quantitative yield) as a white foam.

RD378

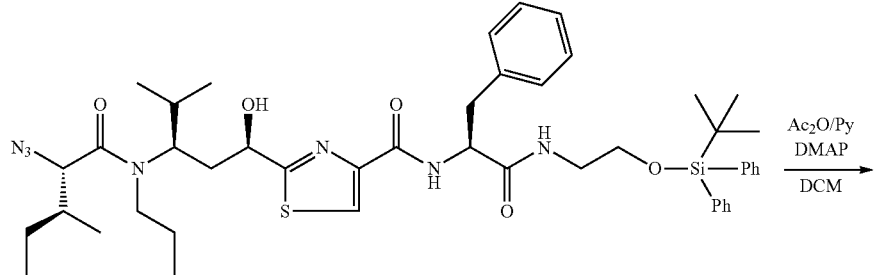

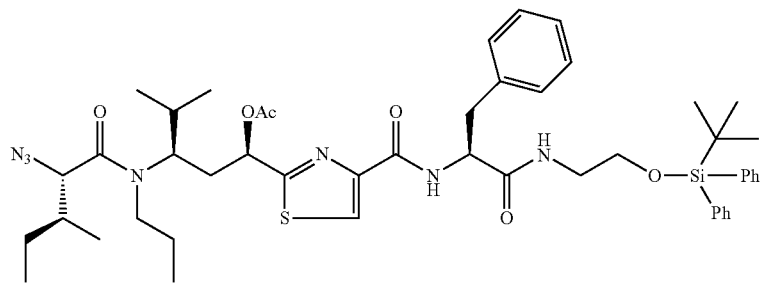

To a solution of RD375 (120 mg, 0.14 mmol) in DCM (10 mL) Ac₂O (57 μL, 0.7 mmol), pyridine (33 μL, 0.35 mmol) and a catalytic amount of DMAP were added. The reaction mixture was stirred for 3 h and the solvent was removed in vacuo. The residue was purified by FC (Hex/AcOEt 6:4) to give 111 mg of RD378 (88% yield) as a white foam.

To a suspension of Mep (19 mg, 0.13 mmol) in DCM (5 mL) HOAt (19 mg, 0.14 mmol), HATU (55 mg, 0.14 mmol), Et₃N (37 μL, 0.26 mmol) and RD381 (95 mg, 0.11 mmol) were added. The reaction mixture was stirred for 4 h. The reaction was washed with H₂O (10 mL), with a saturated

RD381

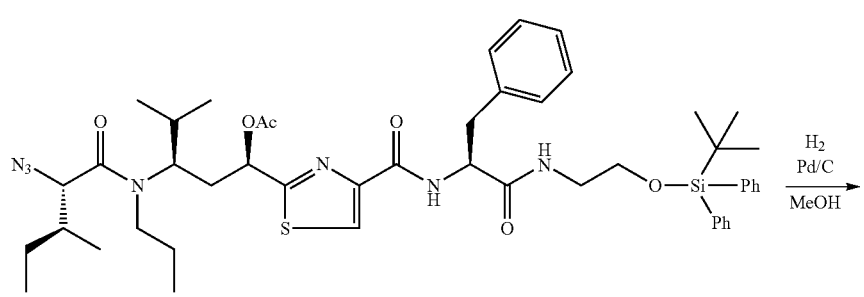

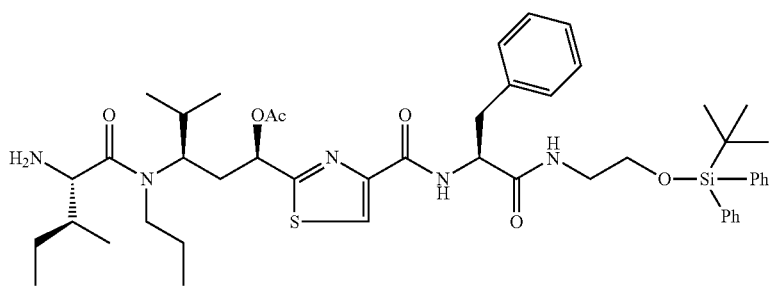

To a solution of RD378 (105 mg, 0.12 mmol) in MeOH (5 mL) Pd/C was added. The reaction mixture was stirred 18 h under a hydrogen atmosphere. The reaction was filtered through celite and the filtrate was concentrated under reduced pressure to give 96 mg of pure RD381 (92% yield) as white foam.

aqueous solution of NaHCO₃ (1×15 mL) and with brine (1×15 mL). After drying over anhydrous Na₂SO₄, and filtration, the solvent was removed in vacuo. The crude product was purified by FC (DCM:MeOH 97:3) to give 74 mg of RD382 (67% yield) as a white foam.

RD382

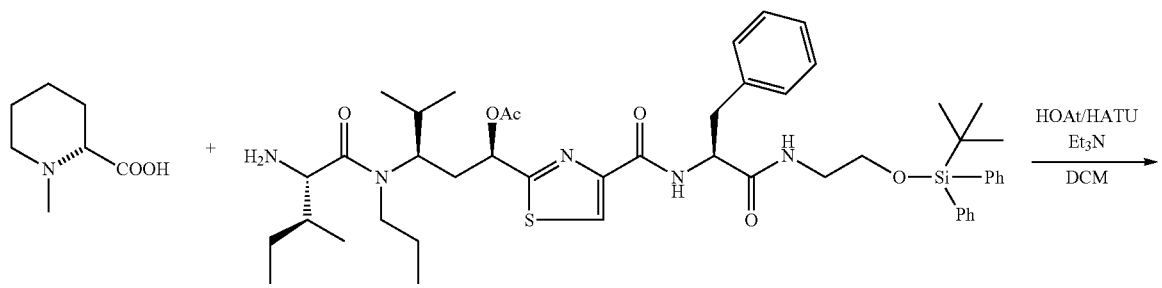

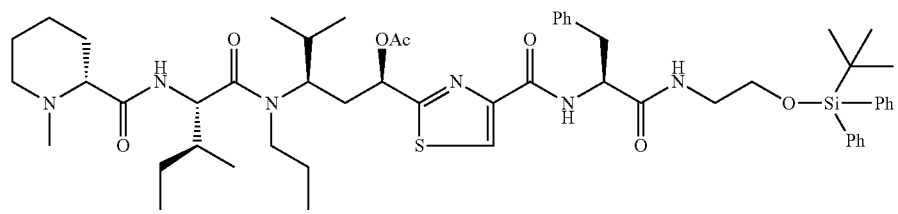

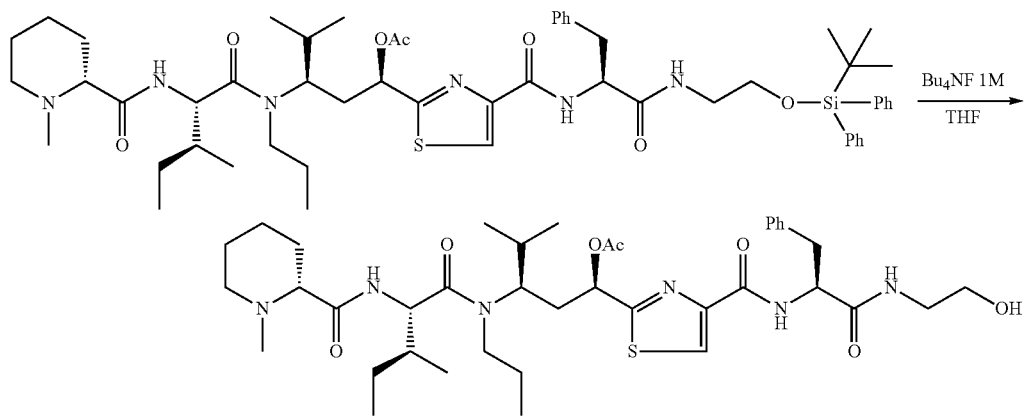

To a solution of RD382 (69 mg, 0.07 mmol) in THF (3 mL) a 1M solution of Bu₄NF in THF (140 µL, 0.14 mmol) was added. The reaction mixture was stirred for 30 min and washed with water (5 mL). The aqueous phase was extracted with AcOEt (1×10 mL). The collected organic phases were dried over anhydrous Na$_2$SO$_4$, filtrated and the solvent was removed in vacuo. The crude was purified by FC (DCM:MeOH 97:3, 9:1) to give 36 mg of RD387 (68% yield) as a white foam.

Synthesis of Various Building Blocks Used in the Preparation of the Compounds of Formula (I)

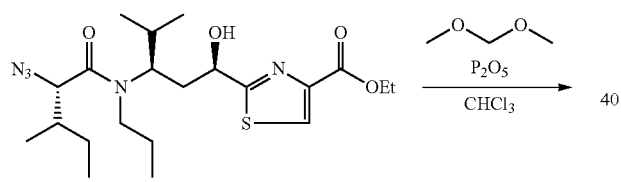

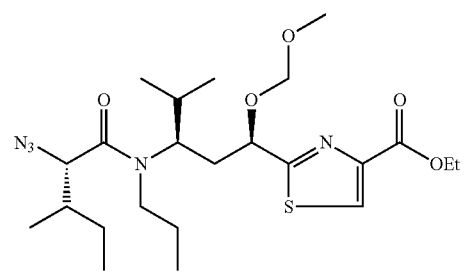

To a solution of dipeptide (200 mg, 0.44 mmol) in a 1:1 mixture of chloroform/formaldehyde dimethyl acetal (2 mL) P$_2$O$_5$ was added portionwise (626 mg, 4.4 mmol). The reaction mixture was poured into a saturated aqueous solution of NaHCO$_3$ (25 mL) and extracted with AcOEt (1×10 mL). The solvent was removed in vacuo and the crude product was purified by flash chromatography (hexane:AcOEt 7:3) to give 154 mg of MSRD356 (70% yield) as a colorless oil.

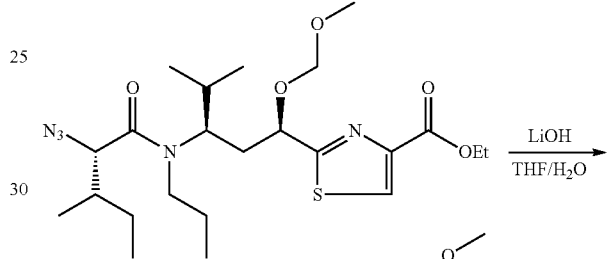

To a solution of MSRD356 (144 mg, 0.29 mmol) in a THF/H$_2$O 4:1 mixture (5 mL), LiOH.H$_2$O (19 mg, 0.43 mmol) was added. The reaction was stirred for 5 h, then H$_2$O (10 mL) and AcOEt (10 mL) were added. The layers were separated and a 1 M solution of HCl was added to the aqueous phase until pH 1-2 was reached. The resulting mixture was extracted whit AcOEt. The organic phase was dried over anhydrous Na$_2$SO$_4$, filtered and the solvent was removed in vacuo to give 119 mg of pure MSRD357 (87% yield) as a white solid.

Compounds RD343, RD358, RD410 and RD483 were synthesized according to analogous procedures using the appropriate starting materials.

Determination of the IC-50 Concentration Against Various Cancer Cell Lines

The anti-proliferative activity of some representative example compounds of the present invention was determined in-vitro using a fluorometric resazurin-based assay. Cancer cell proliferation and viability was quantified upon reduction of non-fluorescent resazurin into the fluorescent dye resorufin by metabolically active cells as described in Strotmann, U. J., et al., The dehydrogenase assay with resazurin: Practical performance as a monitoring system and pH-dependent toxicity of phenolic compounds. *Ecotox. Environ. Safety* 25, 79-89, (1993).

The results are shown in Table 1.
TABLE 1
| Compound | IC50 cell line [nM] HT-29 |
|---|---|
| 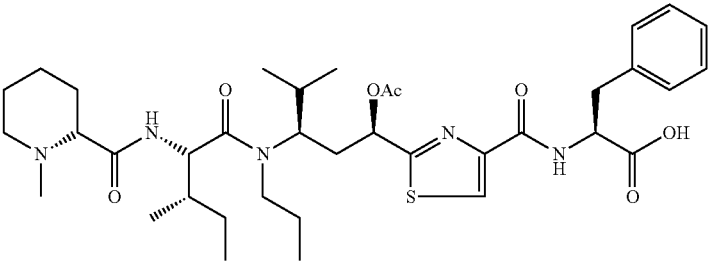 RD333 | 4.5 ± 0.5 |
| 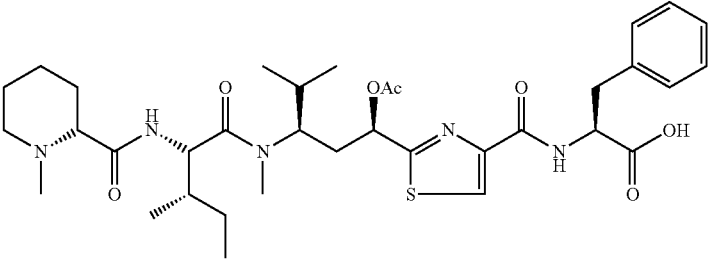 RD343 | 3.2 ± 0.4 |
| 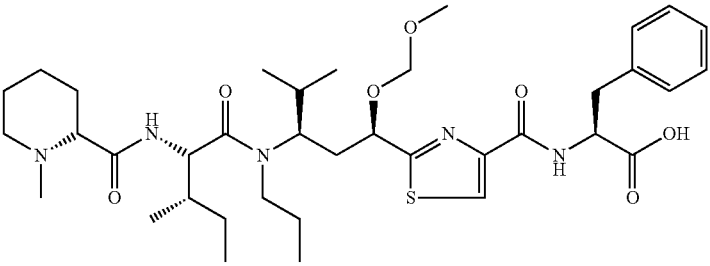 RD358 | 51.1 ± 2.6 |
| 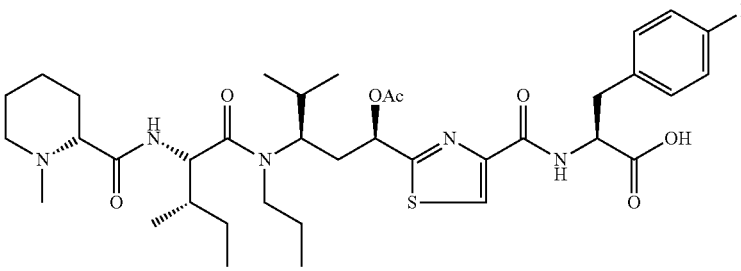 RD410 | 1.0 ± 0.2 |
| 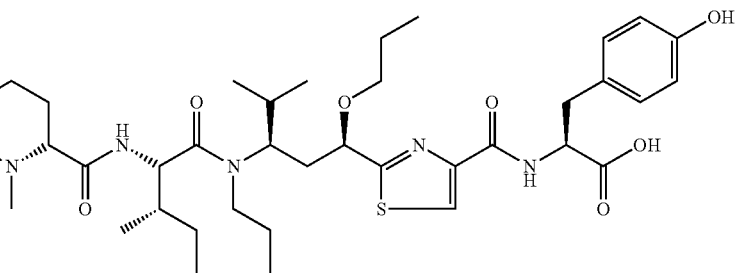 RD483 | 3.1 ± 0.6 |

TABLE 1-continued

| Compound | IC50 cell line [nM] HT-29 |
|---|---|
| 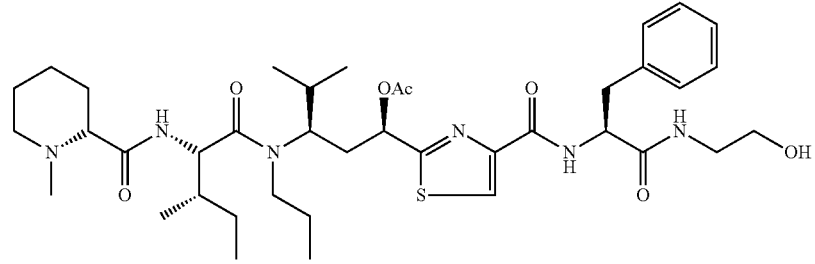 RD387 | 3.9 ± 0.7 |

In general the new molecules of the present invention show an activity against several cancer cell lines between 0.1 to 400 nM.

The invention claimed is:

1. Compound of formula (I):

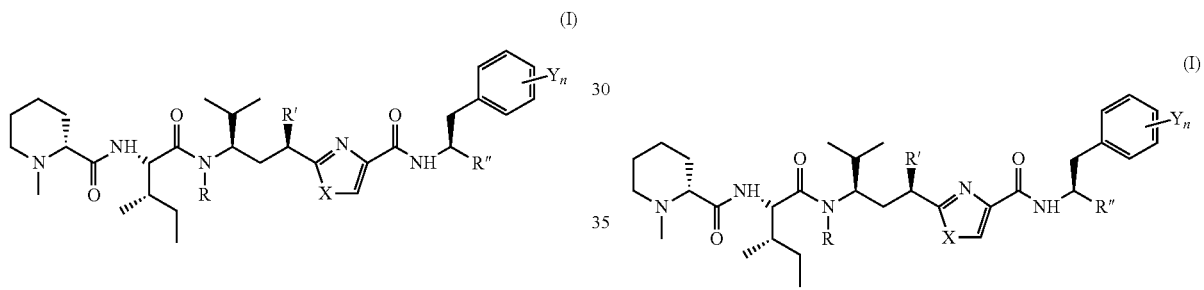

wherein

R is $C_1$-$C_6$ alkyl;

R' is —O—CO-alkyl, alkyl, —O-alkyl, or —O-alkyl-O-alkyl;

R" is a group of formula $CO_2H$, $CO_2R'''$, $CONHR'''$, $CONR_2'''$, with R''' independently being an alkyl, aryl, aralkyl or heteroalkyl group;

X is S or O;

Y is independently optionally substituted alkyl, optionally substituted heteroalkyl, halogen, CN, $NO_2$ or OH;

n is 0, 1, 2, 3, 4 or 5;

or a pharmacologically acceptable salt, solvate, hydrate or a pharmacologically acceptable formulation thereof.

2. Compound according to claim 1, wherein R" is $CO_2H$.

3. Compound according to claim 1, wherein R" is a group of formula $CO_2R'''$, $CONHR'''$ or $CONR_2'''$, with R''' being an alkyl, aryl, aralkyl or heteroalkyl group.

4. Compound according to claim 1, wherein X is S.

5. Compound according to claim 1, wherein Y is independently optionally substituted alkyl, halogen or OH and n is 1.

6. Compound according to claim 1, wherein n is 0.

7. Compound of formula (I)

wherein R is propyl, R' is O-Acetyl, X is S, n is 0 and R" is $CO_2H$.

8. Pharmaceutical composition containing a compound according to claim 1 and optionally one or more carriers or adjuvants.

9. A method for preventing or treating cancer comprising administering a compound of claim 1 to a subject in need thereof, thereby preventing or treating the subject's cancer.

10. A method for preventing or treating cancer comprising administering a pharmaceutical composition of claim 8 to a subject in need thereof, thereby preventing or treating the subject's cancer.

* * * * *